United States Patent [19]

Urbach et al.

[11] Patent Number: 4,668,797
[45] Date of Patent: May 26, 1987

[54] BICYCLIC AMINOACIDS AS INTERMEDIATES AND PROCESSES FOR THEIR PREPARATION

[75] Inventors: Hansjörg Urbach, Kronberg; Rainer Henning, Frankfurt am Main; Volker Teetz, Hofheim am Taunus; Hans Wissman, Bad Soden am Taunus; Reinhard Becker, Wiesbaden, all of Fed. Rep. of Germany

[73] Assignee: Hoechst Aktiengesellschaft, Fed. Rep. of Germany

[21] Appl. No.: 780,937

[22] Filed: Sep. 27, 1985

Related U.S. Application Data

[62] Division of Ser. No. 477,333, Mar. 21, 1983, Pat. No. 4,562,202.

[30] Foreign Application Priority Data

Mar. 23, 1982 [DE] Fed. Rep. of Germany ....... 3210496

[51] Int. Cl.[4] ................. C07D 209/26; C07D 209/18
[52] U.S. Cl. .................................. 548/452; 548/482; 548/502
[58] Field of Search .................... 548/492, 502, 452

[56] References Cited

U.S. PATENT DOCUMENTS 4,508,729 4/1985 Vincent et al. .................... 548/492

Primary Examiner—Richard L. Raymond
Assistant Examiner—D. B. Springer
Attorney, Agent, or Firm—Finnegan, Henderson, Farabow, Garrett & Dunner

[57] ABSTRACT

The invention relates to compounds of the formula I

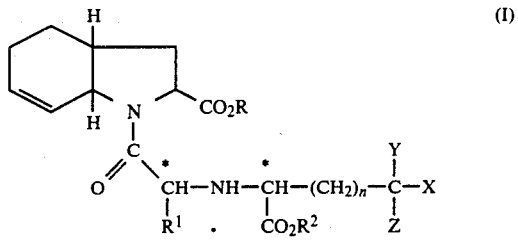

in which
n denotes 0 or 1,
R denotes hydrogen, alkyl or aralky, $R^1$ denotes hydrogen or alkyl, which can optionally be substituted by amino, acylamino or benzoylamino, alkenyl, cycloalkyl, cycloalkenyl, cycloalkylalkyl, aryl or partially hydrogenated aryl, which each can be substituted by alkyl, alkoxy or halogen, arylalkyl or aroylalkyl, both of which can be substituted in the aryl radical as defined in the aforegoing, a monocyclic or bicyclic sulfur or oxygen and/or nitrogen heterocyclic radical, or a side chain of a naturally occurring aminoacid, $R^2$ denotes hydrogen, alkyl, alkenyl or arylalkyl, Y denotes hydrogen or hydroxyl, Z denotes hydrogen or Y and Z together denote oxygen and X denotes alkyl, alkenyl, cycloalkyl, aryl, which is monosubstituted, disubstituted or trisubstituted by alkyl, alkoxy, hydroxyl, halogen, nitro, amino, alkylamino, dialkylamino or methylenedioxy or 3-indolyl, and their physiologically acceptable salts, processes for their preparation, agents containing these and their use as medicaments and also bicyclic amino acids as their intermediates and processes for their preparation.

5 Claims, No Drawings

BICYCLIC AMINOACIDS AS INTERMEDIATES AND PROCESSES FOR THEIR PREPARATION

This is a division of application Ser. No. 477,333, filed Mar. 21, 1983, U.S. Pat. No. 4,562,262, issued Dec. 31, 1985.

The present invention relates to new derivatives of the bicyclic aminoacids of the formula I,

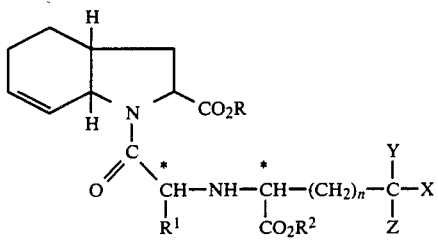

in which
n denotes 0 or 1,
R denotes hydrogen, ($C_1$ to $C_6$)-alkyl or aralkyl having 7 to 9 C atoms,
$R^1$ denotes hydrogen or ($C_1$ to $C_6$)-alkyl, which can optionally be substituted by amino, ($C_1$ to $C_4$)-acylamino, preferably ($C_1$-$C_4$)-alkanoylamino, or benzoylamino, ($C_2$ to $C_6$)alkenyl, ($C_5$ to $C_9$)-cycloalkyl, ($C_5$ to $C_9$)-cycloalkenyl, ($C_5$ to $C_7$)cycloalkyl-($C_1$ to $C_4$)-alkyl, ($C_6$-$C_{10}$)-aryl or partially hydrogenated ($C_6$-$C_{10}$)-aryl, which each can be substituted by ($C_1$ to $C_4$)-alkyl, ($C_1$ or $C_2$)-alkoxy or halogen, ($C_6$-$C_{10}$)-aryl-($C_1$ to $C_4$)-alkyl or ($C_7$-$C_{11}$)-aroyl-$C_1$-alkyl, both of which can be substituted in the aryl radical as defined in the aforegoing, a monocyclic or bicyclic heterocyclic radical having 5 to 7 or 8 to 10 ring atoms respectively, of which 1 to 2 ring atoms represent sulfur or oxygen atoms and/or of which 1 to 4 ring atoms represent nitrogen atoms, or a side chain of a naturally occurring aminoacid,
$R^2$ denotes hydrogen, ($C_1$ to $C_6$)-alkyl, ($C_2$ to $C_6$)-alkenyl or aryl-($C_1$ to $C_4$)-alkyl,
Y denotes hydrogen or hydroxyl,
Z denotes hydrogen or
Y and Z together denote oxygen and
X denotes ($C_1$ to $C_6$)-alkyl, ($C_2$ to $C_6$)-alkenyl, ($C_5$ to $C_9$)-cycloalkyl, ($C_6$-$C_{10}$)-aryl, which can be monosubstituted, disubstituted or trisubstituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkylamino or methylenedioxy, or 3-indolyl, and their physiologically acceptable salts.

Particularly suitable salts are alkali metal and alkaline earth metal salts, salts with physiologically tolerated amines and salts with inorganic or organic acids, such as, for example, HCl, HBr, $H_2SO_4$, maleic acid or fumaric acid.

In this context and the following text, aryl is to be understood preferably as optionally substituted phenyl or naphthyl. Alkyl can be straight-chain or branched.

Two possible configurations of the carboxyl group are suitable in the preferred configuration of the H atoms on C-3a and C-7a of the bicycle, namely those in the exo position (part formula Ia) and the endo position (part formula Ib) of the carboxyl group.

The endo position of the carboxyl group on C-2 is defined such that the carboxyl group is turned towards the direction of the 6-membered ring of the bicycle, i.e. the concave side of the bicycle (part formula Ib).

Accordingly, the exo position of the carboxyl group on C-2 is defined such that the carboxyl group is oriented in the direction of the relevant bridgehead H atoms (part formula Ia).

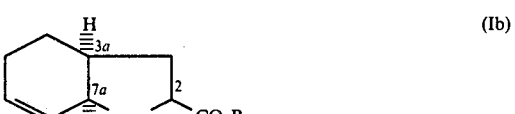

Compounds of the formula I have chiral C atoms in positions C-2, C-3a, C-7a and in the C atoms in the side chain marked with an asterisk. The invention relates to both the R and S configurations at all centers. The compounds of the formula I can thus be present as optical isomers, as diastereomers as racemates or as mixtures of these. However, the compounds of the formula I are preferred in which the C atom 2 in the bicyclic ring system and the C atoms in the side chain marked with an asterisk (*) have the S configuration.

Those compounds of the formula I are particularly preferred in which
n denotes 1,
R denotes hydrogen or alkyl having 1 to 4 C atoms,
$R^1$ denotes hydrogen, ($C_1$ to $C_3$)-alkyl, ($C_2$ or $C_3$)-alkenyl, benzyl, phenethyl, 4-aminobutyl or benzoylmethyl,
$R^2$ denotes hydrogen, ($C_1$ to $C_4$)-alkyl or benzyl and,
X denotes phenyl, which can be monosubstituted or disubstituted, or in the case of methoxy, trisubstituted, by ($C_1$ or $C_2$)-alkyl, ($C_1$ or $C_2$)-alkoxy, hydroxyl, fluorine, chlorine, bromine, amino, ($C_1$ to $C_4$)-alkylamino, di-($C_1$ to $C_4$)-alkylamino, nitro or methylenedioxy,
in particular those compounds of the formula I in which
n denotes 1, R denotes hydrogen, $R^1$ denotes methyl, X denotes phenyl, $R^2$ denotes hydrogen or ethyl, the bicycle has the cis configuration, the carboxyl group is oriented exo or endo and the chiral C atoms, which are identified with an asterisk (*), and C atom 2 have the S configuration.

The invention further relates to processes for the preparation of the compounds of the formula I. One process variant comprises reacting, by the known methods of amide formation in peptide chemistry, a compound of the formula II,

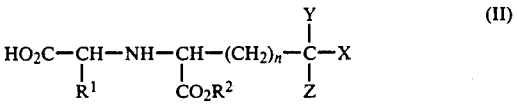

wherein
n, $R^1$, $R^2$, X, Y and Z have the meanings as in formula I, with a compound of the formula III,

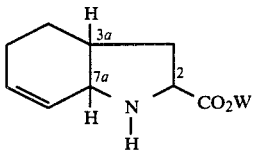

in which

W denotes hydrogen or a radical which can be split off by acid, in particular a tert.-butyl radical, and then optionally splitting off the radical W by acid treatment and optionally also splitting off the radical $R^2$ by additional acid or base treatment, the free carboxylic acids being obtained in each case.

Further synthetic processes for the preparation of the compounds of the formula I, in which Y and Z together denote oxygen, comprise reacting, in a known manner in a Michael reaction (Organikum, 6th edition, page 492, 1967), a compound of the formula IV,

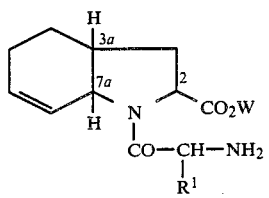

in which $R^1$ has the meaning as in formula I and W has the meaning as in formula III, with a compound of the formula V $$R^2O_2C-CH=CH-CO-X \qquad (V)$$

wherein $R^2$ and X have the meanings as in formula I, and optionally splitting off the radical W and/or the radical $R^2$, as described above, or reacting, in a known manner in a Mannich reaction (Bull. Soc. Chim. France 1973, page 625), a compound of the abovementioned formula IV with a compound of the general formula VI, wherein $R^2$ has the meaning as in formula I, and with a compound of the general formula VII, $$OHC-CO_2R^2 \qquad (VI)$$
$$X-CO-CH_3 \qquad (VII)$$

wherein

X has the meaning as in formula I, and then optionally splitting off the radical W and/or the radical $R^2$ as described above with formation of the free carboxyl groups.

Furthermore, compounds of the formula I, with Y and Z each being hydrogen, can also be prepared in a manner such that a compound of the abovementioned formula IV is reacted, in accordance with the procedure described in J. Amer. Chem. Soc. 93, 2897 (1971), with a compound of the formula VIII,

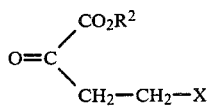

wherein $R^2$ and X have the meanings as in formula I, the Schiff's bases obtained are reduced and then the radical W and/or the radical $R^2$ are optionally split off as described above, with formation of the free carboxyl groups. The reduction of the Schiff's bases can be carried out electrolytically or with reducing agents, such as, for example, sodium borohydride or sodium cyanoborohydride.

Compounds of the formula I, with Y being hydroxyl and Z being hydrogen, can also be obtained, for example, by reduction of a compound I, with Y and Z together being oxygen, obtained according to the above procedures. This reduction can be carried out with a reducing agent, such as sodium borohydride and other complex boranates or, for example, borane-amine complexes.

Compounds of the formula I, in which R represents hydrogen, can optionally be converted by methods known per se into their esters of the formula I, wherein R denotes ($C_1$ to $C_6$)-alkyl or ($C_7$-$C_9$)-aralkyl.

The invention also relates to compounds of the formula III,

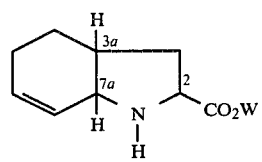

in which the H atoms on the C atoms 3a and 7a have the cis configuration relative to one another and the group $-CO_2W$ on C atom 2 is oriented exo and or endo to the bicyclic ring system and wherein W denotes hydrogen or a radical which can be split off by acid.

These compounds serve according to the invention as starting materials for the synthesis of compounds of the formula I and can, according to the invention, be prepared by the following procedure:

Compounds of the formula IX,

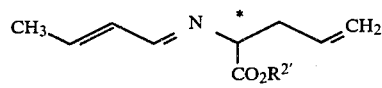

in which $R^{2'}$ denotes ($C_1$ to $C_6$)-alkyl or ($C_7$ to $C_8$)-aralkyl, are reacted with acylating agents, which transfer the group $-CO-R^3$, wherein the radical $R^3$ represents ($C_1$ to $C_6$)-alkyl, ($C_5$ to $C_9$)-cycloalkyl, ($C_2$ to $C_6$)-alkenyl, ($C_1$ to $C_6$)-alkoxy, aryl, aryloxy, aryl-($C_1$ to $C_4$)-alkyl or aryl-($C_1$ to $C_4$)-alkoxy, to give compounds of the formula X,

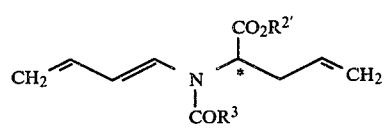

in which $R^{2'}$ and $R^3$ have the foregoing meaning, the latter are cyclized to give a mixture of stereoisomeric compounds of the formula XI,

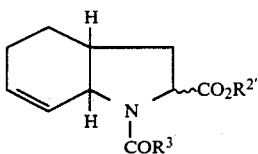

(XI)

in which $R^{2'}$ and $R^3$ have the foregoing meaning and the hydrogen atoms on the bridgehead C atoms have the cis configuration, this mixture of stereoisomers, in which pairs of diastereomers are present, depending on whether the starting compounds of the formula IX had the R or S configuration or were racemic, of the formula XIb and d or XIa and c, or mixtures of the formulae XIa–d, respectively,

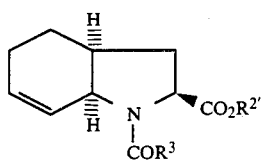

(XIa)

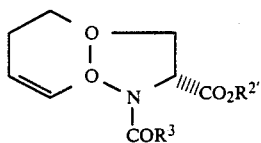

(XIb)

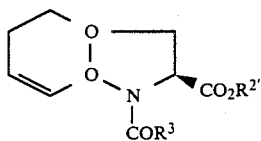

(XIc)

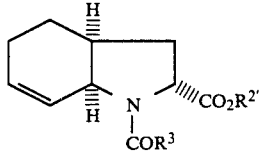

(XId)

in which $R^{2'}$ and $R^3$ each have the foregoing meaning, is hydrolyzed, optionally after previous separation into enantiomers, pairs of diastereomers or racemates, to give compounds of the formula III, in which W represents hydrogen, and the latter are optionally esterified to give compounds of the formula III, in which W represents a radical which can be split off by acid.

The synthesis of compounds of the formula IX starts from an allylglycine ester of the formula XII,

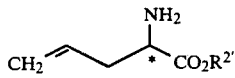

(XII)

wherein $R^{2'}$ is ($C_1$ to $C_6$)-alkyl or ($C_7$ to $C_8$)-aralkyl, preferably ($C_1$ to $C_4$)-alkyl or benzyl. The allylglycine ester can be employed in the synthesis as the racemic compound or as optically pure R or S form. The synthesis of the racemic allylglycine is described in Monatshefte der Chemie 85, 1071 (1954); that of the R and the S compounds in J. biol. Chem. 223, page 40 (1955). The esterification is carried out by known methods of organic chemistry. The preparation of the ethyl ester is described in the article in Monatschefte der Chemie.

The compound of the formula XII is reacted with crotonaldehyde in an organic solvent, with separation out of water, to give the Schiff's base of the formula IX. The reaction is carried out at temperatures in the range from $-40°$ to $+80°$ C., preferably at $+20°$ C. Aprotic solvents, such as, for example, benzene, toluene, carbon tetrachloride or chloroform are used. The water of reaction is removed from the reaction equilibrium with a water-binding agent, such as, for example, $MgSO_4$, $Na_2SO_4$, molecular sieves or an organic auxiliary, such as, for example, orthoformates or by means of azeotropic separation out of water.

The Schiff's base is preferably acylated in an aprotic solvent, such as, for example, methylene chloride, chloroform, toluene or dimethylformamide, in the presence of a base, such as, for example, triethylamine, collidine, pyridine or other amines, with an acylating agent, such as, for example, an acid chloride, to give the dienamide of the formula X. The reaction is carried out at temperatures in the range from $-80°$ to $+40°$ C. Preferably, the reaction is started at $-80°$ C. and completed at $20°$ C.

In the acylating agent which transfers the group $-CO-R^3$, $R^3$ preferably denotes phenyl, tert.-butoxy, methyl, methoxy or ethoxy. The compound of the formula X is preferably heated in a high boiling organic solvent and cyclized, in an intramolecular Diels-Alder reaction, to give the bicyclic amino acid derivatives XIa–d, which are produced as a mixture of stereoisomers.

Those solvents can be used which boil in a temperature range between 80° and 250° C., such as, for example, toluene, xylene or dichlorobenzene. The thermolysis is also possible with a lower boiling solvent in a pressure apparatus. Preferably, the thermolysis is carried out in a temperature range between 100° and 180° C. under normal pressure. In order to deactivate the glass surface of the reaction vessel, if appropriate, bistrimethylsilylacetamide or customary deactivating compounds or acid traps and a radical trap such as, for example, tert.-butylcatechol to suppress radical side reactions are added.

The endo-cis compounds XIa and XIb and the exo-cis compounds XIc and XId are each present as racemates when the racemic allylglycine ester XII is used. On using the allylglycine ester with the S configuration as the starting compound, the aminoacid derivatives XIa having the cis-endo-S configuration and XIc having the cis-exo configuration are obtained, the S configuration relating to the C atom 2. Correspondingly, on using the allylglycine ester with the R configuration, the aminoacid derivatives XIb and XId having the R configuration at carbon 2 are obtained. The racemates XIa/XIb and XIc/XId or the diastereomers XIa and XIc or XIb and XId can be separated, for example, by fractional crystallization or by column chromatography on silica gel by customary methods. The racemates or the optically pure diastereomers can be employed in the further reactions.

The aminoacids of the formula III, wherein W denotes hydrogen, are obtained by acid or alkaline hydrolysis. The aminoacids can optionally be esterified. The preferred tert.-butyl esters of the aminoacids of the formula III (W=tert.-butyl) are obtained by the methods customary in peptide chemistry, such as, for example, by reaction of the acids with isobutylene in an inert organic solvent (for example dioxane) in the presence of acids (such as, for example, sulfuric acid). The following process has been found to be particularly advantageous: the appropriate aminoacid is acylated on the nitrogen with a group which can be split off by base, such as, for example, the methylsulfonylethoxycarbonyl group (=MSC), Tesser, Balvert-Geers, Int. J. Pept. Protein Res. 7, 295 (1975). The carboxylic acid is reacted, in the neutral to weakly basic pH range, with tert.-butanol in an organic solvent, such as, for example, pyridine, in the presence of propylphosphonic anhydride to give the corresponding tert.-butyl ester. The tert.-butyl ester of the formula III (W=tert.-butyl) is obtained by splitting off the MSC protective group in the strongly alkaline pH range with alkali in an aqueous solvent.

The compounds of the formula II, with n being 1, Y and Z being hydrogen, $R^1$ being methyl and $R^2$ being methyl or ethyl and X being phenyl, used as starting materials for the preparation of the compounds of the formula I, are known (European Patent Application No. 37,231). The compounds of the formula II can be prepared by various procedures. One synthetic variant starts from a ketone of the abovementioned formula VII, which is reacted, by known procedures in a Mannich reaction, with a compound of the abovementioned formula VI, together with aminoacid esters of the formula XIII,

(XIII)

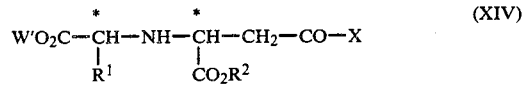

(XIV)

wherein $R^1$ has the abovementioned meaning and W' denotes a radical which can be split off by hydrogenolysis or by acid, in particular a benzyl or a tert.-butyl radical, to give a compound of the formula XIV, wherein $R^1$, $R^2$, X and W' have the abovementioned meanings, with the restriction that when W' denotes a radical which can be split off by hydrogenolysis, in particular benzyl, $R^2$ may not have the meaning of W'. If the radical W' is split off by hydrogenolysis using, for example, palladium, compounds of the formula II with Y and Z being hydrogen are obtained on uptake of 3 mole-equivalents of hydrogen. If the uptake of hydrogen is stopped at 1 mole-equivalent, compounds of the formula II with n being 1 and Y and Z together being oxygen are obtained, and these are also obtained when the radical W' of the formula XIV is split off with acids, such as, for example, trifluoroacetic acid or hydrochloric acid, in an inert organic solvent, such as, for example, dioxane.

Compounds of the formula XIV can also be obtained by Michael additions of a compound of the abovementioned formula V with a compound of the abovementioned formula XIII by known procedures. This process is particularly suitable for the preparation of those compounds of the formula XIV in which $R^1$ denotes methyl, $R^2$ denotes ethyl and X denotes aryl.

The compounds of the formula XIV are produced as mixtures of diastereomers. Preferred diastereomers of the formula XIV are those in which the chiral C atoms marked with an asterisk each have the S configuration. These can be separated out, for example, by crystallization or by chromatography, for example, on silica gel.

On subsequently splitting off the radical W', the configurations of the chiral C atoms are retained.

The compounds of the abovementioned formula IV used as starting materials for the preparation of the compounds of the formula I are obtained by known procedures from the compounds of the abovementioned formula III by reaction with a N-protected 2-aminocarboxylic acid of the formula XV,

(XV)

wherein V is a protective group and $R^1$ has the abovementioned meaning. An example of a suitable protective group V, which is split off again after the reaction is complete, is tert.-butoxycarbonyl.

The reaction of a compound of the formula II with a compound of the formula III to prepare a compound of the formula I is carried out in accordance with a condensation reaction known in peptide chemistry, dicyclohexylcarbodiimide and 1-hydroxybenzotriazole, for example, being added as the condensing agent. On subsequently splitting off the radical W with acid, trifluoroacetic acid or hydrogen chloride are preferably employed as the acids.

In the reactions for the preparation of the compounds of the formulae III, IV and I, described above, the configurations of the intermediate products at the bridgehead C atoms 3a and 7a are retained in each case.

The compounds of the formula III obtained according to the procedure described above are produced as a mixture and can be separated from one another, for example, by recrystallization or by chromatography.

The compounds of the formula III are produced as racemic mixtures and can be employed as such in the further syntheses described above. However, they can also be employed as the pure enantiomers after separation of the racemates into the optical antipodes using customary methods, for example via salt formation with optically active bases or acids. The pure enantiomers can also be obtained.

If the compounds of the formula I are produced as racemates, these can also be resolved into their enantiomers by the customary methods, such as, for example, via salt formation with optically active bases or acids, or can be separated by chromatography.

The compounds of the formula I according to the invention are, if R is hydrogen, in the form of internal salts. Since they are amphoteric compounds, they can form salts with acids or bases. These salts are prepared in a customary manner by reaction with one equivalent of acid or base.

The compounds of the formula I and their salts have long-lasting and powerful hypotensive activities. They are strong inhibitors of the angiotensin converting enzyme (ACE inhibitors). They can be employed to control high blood pressure of various etiologies. It is also possible to combine them with other compounds having hypotensive, vasodilator or diuretic activity. Typical representatives of these classes of active compounds are described, for example, in Erhardt-Ruschig, Arzneimittel (Drugs), 2nd edition, Weinheim, 1972. They can be used intravenously, subcutaneously or perorally.

The dosage on oral administration is 1–100 mg, preferably 1–40 mg, for a single dose for an adult patient of normal weight, which corresponds to a dose of 0.013–1.3 mg/kg/day, preferably 0,013–0,53 mg/kg/day. This can also be increased in severe cases, since no toxic properties have been observed hitherto. A decrease in the dose is also possible and is particularly appropriate when diuretics are administered concurrently.

The compounds according to the invention can be administered orally or parenterally in an appropriate pharmaceutical formation. For a form for oral use, the active compounds are mixed with the additives customary for this purpose, such as vehicles, stabilizers or inert diluents and converted by customary methods into suitable forms for administration, such as tablets, coated tablets, hard capsules, aqueous, alcoholic or oily suspensions or aqueous, alcoholic or oily solutions. Inert vehicles which can be used are, for example, gum arabic, magnesium carbonate, potassium phosphate, lactose, glucose or starch, particularly corn starch. In this context, the formulation can either be as dry or as moist granules. Examples of suitable oily vehicles or solvents are plant and animal oils, such as sunflower oil or cod-liver oil.

For subcutaneous or intravenous administration, the active compounds or their physiologically tolerated salts are converted into solutions, suspensions or emulsions, if desired together with the substances customary for this purpose such as solubilizers, emulsifiers or other auxiliaries. Examples of suitable solvents for the new active compounds and the corresponding physiologically tolerated salts are: water, physiological saline or alcohols, for example ethanol, propanediol or glycerol, additionally also sugar solutions, such as glucose or mannitol solutions, or also a mixture of the various solvents mentioned.

The extremely high activity of the compounds according to formula I is demonstrated by the pharmacological data in the following tables:

intraduodenal administration to the anaesthetized rat, 50% inhibition of the pressor reaction induced by 310 ng of angiotensin I 30 min. after administration in the dose . . . =$ED_{50}$:

TABLE 1

(H atoms on C-3a and C-7a in formula I have the cis configuration, the carboxyl group on C-2 has the endo configuration and the C atoms identified with* and C-2 have the S configuration, unless otherwise specified in the table)

| n | X | Y | Z | $R^2$ | $R^1$ | R | $ED_{50}$ (µg/kg) |
|---|---|---|---|---|---|---|---|
| 1 | phenyl | H | H | $C_2H_5$ | $CH_3$ | H | 40 |
| 1 | phenyl | H | H | H | $CH_3$ | H | 600 |
| 1 | phenyl | H | H | $C_2H_5$ | $CH_3$ | H | 80(R,S— configuration on C-2 in formula I) |
| 1 | phenyl | | —O— | $C_2H_5$ | $CH_3$ | H | 390 |

The symbols n, X, Y, Z, R, $R^1$ and $R^2$ relate to the compounds of the formula I.

TABLE II (H atoms on C-3a and C-7a in formula I have the cis configuration, the carboxyl group has the exo configuration and the C atoms identified with* and C-2 have the S configuration)

| n | X | Y | Z | $R^2$ | $R^1$ | R | $ED_{50}$ (µg/kg) |
|---|---|---|---|---|---|---|---|
| 1 | phenyl | H | H | $C_2H_5$ | $CH_3$ | H | 70 |
| 1 | phenyl | H | H | H | $CH_3$ | H | 700 |
| 1 | phenyl | | —O— | $C_2H_5$ | $CH_3$ | H | 500 |

The symbols n, X, Y, Z, R, $R^1$ and $R^2$ relate to the compounds of the formula I.

The following examples serve to illustrate the invention, but without restricting it to the compounds mentioned as being representatives.

The $^1$H NMR data reported in the following examples were found by measurement in $CDCl_3$ and are reported in δ(ppm).

EXAMPLE 1

N-(1S-carboethoxy-3-phenylpropyl)-S-alanyl-cis-2,3,3a,4,5,7a-hexahydro[1H]indole-2R,S-endo-carboxylic acid (a) Ethyl ester of N-benzoyl-N-(1,3-butadienyl)-R,S-allyl-glycine 28.6 g of R,S-allylglycine ethyl ester were dissolved in 140 ml of toluene, and 14.0 g of crotonaldehyde were added. After adding 30 g of anhydrous magnesium sulfate, the mixture was stirred at room temperature for 3 hours. The magnesium sulfate was then filtered off with suction and the toluene was removed in vacuo. Residue: 44.4 g of oil.

750 ml of methylene chloride were cooled down to −70° C. and 44.4 g of triethylamine and 28.1 g of benzoyl chloride were added. To this were added the 44.4 g of Schiff's base obtained above. The mixture was stirred at −75° C. for 2 hours. It was then allowed to warm to 0° C. The solvent was removed in a rotary evaporator at room temperature. The residue was then taken up in toluene, washed with water, dried and the toluene was removed in a rotary evaporator. The residue was filtered through a short column of silica gel (500 ml). Methylene chloride was used to elute. After evaporating off the methylene chloride, 49 g of ethyl ester of N-benzoyl-N-(1,3-butadienyl)-R,S-allylglycine were obtained.

$^1$H NMR data: 1.1–1.4 (t, 3H), 2.7–3.1 (m, 2H), 4.0–4.5 (m, 3H), 4.8–6.8 (m, 8H), 7.3–7.6 (s, 5H).

(b) Ethyl N-benzoyl-cis-2,3,3a,4,5,7a-hexahydro[1H]indole-2R,S-endo-carboxylate 49 g of N-benzoyl-N-(1,3-butadienyl)-R,S-allylglycine ethyl ester were dissolved in 1,000 ml of xylene, and 0.1 g of tert.-butylcatechol and 5 drops of bistrimethylsilylacetamide were added. The mixture was heated to reflux under nitrogen for 6 hours, a further 0.1 g of tert.-butylcatechol and 5 drops of bistrimethylsilylacetamide being added after 3 hours. The xylene was removed in a rotary evaporator and 43 g of an oily residue remained.

70 g of oil were chromatographed on silica gel with toluene/ethyl acetate 4:1. 53 g of ethyl N-benzoyl-cis-2,3,3a,4,5,7a-hexahydro[1H]indole-2R,S-endocarboxylate (Rf: 0.18) were obtained as an oil and 7.5 g of ethyl N-benzoyl-cis-2,3,3a,4,5,7a-hexahydro[1H]indole-2R,S-exo-carboxylate (Rf: 0.26, melting point: 96°–98° C.) were obtained.

Both compounds are in the form of racemates.

(c)
Cis-2,3,3a,4,5,7a-hexahydro[1H]indole-2R,S-endo-carboxylic acid 1.5 g of ethyl N-benzoyl-cis-2,3,3a,4,5,7a-hexahydro[1H]indole-2-endo-R,S-carboxylate were dissolved in 10 ml of ethanol. 0.35 g of potassium hydroxide dissolved in 5 ml of water was added to this. The mixture was stirred at room temperature for 2½ hours, diluted with water and extracted with ethyl acetate. The aqueous solution was acidified with 2N hydrochloric acid and again extracted with ethyl acetate. After drying and evaporation on a rotary evaporator, 0.9 g of N-benzoyl-cis-2,3,3a,4,5,7a-hexahydro-[1H]indole-2-endo-carboxylic acid of melting point 153°–154° C. was obtained.

13.4 g of the N-benzoyl carboxylic acid were dissolved in a mixture of 200 ml of 2N hydrochloric acid and 67 ml of ethanol and heated under nitrogen at a bath temperature of 110° C. for 22 hours. The alcohol was removed in vacuo and the aqueous phase was extracted with methylene chloride. The pH was then adjusted to 7.0 with concentrated sodium hydroxide solution and the solution was evaporated to dryness in vacuo. The residue was taken up in methylene chloride/methanol, salt was removed by filtration, the filtrate was evaporated and recrystallized from ethanol/ether. Yield: 7.0 g, melting point: 220° C. (decomposition).

(d)
N-(1S-carboethoxy-3-phenylpropyl)-S-alanyl-cis-2,3,3a,4,5,7a-hexahydro[1H]indole-2R,S-endo-carboxylic acid 0.84 g of N-(1S-carboethoxy-3-phenylpropyl)-S-alanine, 0.69 g of N-hydroxysuccinimide and 0.66 g of dicyclohexylcarbodiimide were dissolved in 8 ml of dry dimethylformamide at 0° C. The solution was then stirred at room temperature for 3 hours. A solution of 0.5 g of cis-2,3,3a,4,5,7a-hexahydro[1H]indole-2R,S-endo-carboxylic acid in 10 ml of dimethylformamide and 10 ml of water, in the presence of 0.27 g of concentrated sodium hydroxide solution, was then added. The mixture was stirred at room temperature for 12 hours, the dicyclohexylurea formed was filtered off with suction and the filtrate was neutralized with 2N hydrochloric acid. It was then evaporated to dryness in vacuo, taken up in ethyl acetate, insolubles were filtered off and the ethyl actate solution was evaporated in vacuo. The residue was purified over silica gel, eluting with methylene chloride/methanol 9:1. Yield: 0.13 g (Rf: 0.74).

EXAMPLE 2

N-(1S-carboethoxy-3-phenylpropyl)-S-alanyl-cis-2,3,3a,4,5,7a-hexahydro[1H]indole-2S-endo-carboxylic acid The compound was obtained by separating the mixture of diastereomers from Example 1d on a sufficient amount of silica gel, eluting with methylene chloride/methanol 9:1. Rf: 0.65.

EXAMPLE 3

N-(1S-carboethoxy-3-phenylpropyl)-S-alanyl-cis-2,3,3a,4,5,7a-hexahydro[1H]indole-2R-endo-carboxylic acid The compound was obtained by separating the mixture of diastereomers from Example 1d on a sufficient amount of silica gel, eluting with methylene chloride/methanol 9:1. Rf: 0.8.

EXAMPLE 4

Tert.-butyl cis-2,3,3a,4,5,7a-hexahydro[1H]indole-2R,S-endo-carboxylate 3.35 g of cis-2,3,3a,4,5,7a-hexahydro[1H]indole-2R,S-endo-carboxylic acid were dissolved in 50 ml of dimethylformamide, and 5.3 g of methylsulfonylethyl succinimidocarbonate and 2.3 g of ethylmorpholine were added. The mixture was allowed to stand at room temperature for 12 hours, the solvent was evaporated off in vacuo and the residue was dissolved in ethyl acetate. The ethyl acetate solution was extracted by shaking with saturated sodium bicarbonate solution, this was adjusted to pH 3.5 with 2N hydrochloric acid, and extracted several times with ethyl acetate. After drying, the combined ethyl acetate solutions were evaporated. The residue obtained was 8.5 g of N-methylsulfonylethyloxycarbonyl-cis-2,3,3a,4,5,7a-hexahydro[1H]indole-2R,S-endo-carboxylic acid, which was dissolved in 10 ml of pyridine. To this were added, at 0° C., 10 ml of tert.-butanol and 12 ml of a 50% strength solution of propylphosphonic anhydride in methylene chloride. The mixture was stirred at 40° C. for 6 hours, 200 ml of ethyl acetate were added and potassium bisulfate solution was added until a pH of 3.5 was reached. The mixture was extracted with ethyl acetate, the ethyl acetate solution was washed with water, dried and evaporated in vacuo. The oil remaining was purified on silica gel, eluting with ethyl acetate. The tert.-butyl ester was obtained as an oil.

$^1$H NMR data: 1.4 (s, 9H), 1.0–2.8 (m, 1H), 2.9 (s, 3H), 3.1–3.5 (m, 2H), 3.7–4.8 (m, 4H), 5.6–5.9 (m, 2H), 1.35 g of tert.-butyl ester was dissolved in 15 ml of methanol and 1.5 ml of water. The pH was adjusted to 13 with 2N sodium hydroxide solution and the mixture was stirred at room temperature for 2 hours. It was then neutralized with 2N hydrochloric acid, the methanol was evaporated in vacuo, the aqueous phase was extracted with ethyl acetate, and the ethyl acetate solution was washed with water, dried and evaporated. The oily residue was purified on silica gel, eluting with ethyl acetate.

0.3 g of tert.-butyl cis-2,3,3a,4,5,7a-hexahydro [1H]indole-2R,S-end-carboxylate was thus obtained as an oil.

$^1$H NMR data: 1.4 (s, 9H), 1.0–2.7 (m, 8H), 3.2–4.9 (m, 2H), 5.8 (d, 2H).

EXAMPLE 5

Tert.-butyl N-(1S-carboethoxy-3-phenylpropyl)-S-alanyl-cis-2,3,3a,4,5,7a-hexahydro[1H]indole-2S-endocarboxylate 0.28 g of N-(1S-carboethoxy-3-phenylpropyl)-S-alanine was dissolved in 4 ml of dimethylformamide. Then 0.15 g of hydroxybenzotriazole and 0.22 g of dicyclohexylcarbodiimide were added at room temperature. The mixture was stirred at room temperature for 4 hours. Then 0.24 g of tert.-butyl ester from Example 4 was added and the mixture was stirred at room temperature for 20 hours. It was diluted with ethyl acetate, the urea was filtered off with suction and the filtrate was evaporated in vacuo. The residue was taken up in ethyl acetate and the ethyl acetate solution was washed with bicarbonate solution, dried and evaporated. The oily residue (0.6 g) was separated into the diastereomers on silica gel, eluting with ethyl acetate/cyclohexane 2:1.

0.24 g of the tert.-butyl ester having the 2S-endo configuration was obtained. (Rf: 0.45, m/e:484).

$^1$H NMR data: 1.4 (s, 9H), 0.8–3.8 (m, 20H), 3.9–4.6 (m, 4H), 5.4–6.0 (m, 2H), 7.2 (s, 5H).

EXAMPLE 6

Tert.-butyl N-(1S-carboethoxy-3-phenylpropyl)-S-alanyl-cis-2,3,3a,4,5,7a-hexahydro[1H]indole-2R-endo-carboxylate This ester was obtained on chromatography, on silica gel as described in Example 5, of the mixture of diastereomers from Example 5. Ethyl acetate/cyclohexane was used to elute. Yield: 0.16 g (Rf: 0.3; m/e=484).

EXAMPLE 7

N-(1S-carboethoxy-3-phenylpropyl)-S-alanyl-cis-2,3,3a,4,5,7a-hexahydro[1H]indole-2R-endo-carboxylic acid trifluoroacetate 0.16 g of the tert.-butyl ester obtained in Example 6 was dissolved in 1 ml of trifluoroacetic acid at 0° C. and the mixture was stirred at this temperature for 3 hours. The trifluoroacetic acid was evaporated off in vacuo and the residue was crystallized from diisopropyl ether. Yield of trifluoroacetate: 0.08 g of melting point: 120°–121° C. The trifluoroacetate can be converted into the amino acid using basic ion exchangers (OH$^-$form) in methanol/water 60:40.

EXAMPLE 8

N-(1S-carboethoxy-3-phenylpropyl)-S-alanyl-cis-2,3,3a,4,5,7a-hexahydro[1H]indole-2S-endo-carboxylic acid trifluoroacetate 0.24 g of the tert.-butyl ester described in Example 5 was dissolved in 1.5 ml of trifluoroacetic acid at 0° C. and the mixture was stirred at this temperature for 5 hours. The trifluoroacetic acid was then removed in vacuo and the residue was crystallized from diisopropyl ether/petroleum ether. Yield: 0.1 g; m/e (after silylation) 500.

EXAMPLE 9

N-(1S-carboethoxy-3-phenylpropyl)-S-alanyl-cis-2,3,3a,4,5,7a-hexahydro[1H]indole-2S-endo-carboxylic acid hydrochloride A solution of 0.6 g of tert.-butyl ester from Example 5 in 5 ml of methylene chloride was saturated with dry hydrogen chloride gas and allowed to stand at 20°–25° C. for 16 hours. The solution was evaporated in vacuo. The residue was saturated with diisopropyl ether and filtered off with suction.

Yield: 0.4 g $^1$H NMR data: 0.9–3.0 (m, 17H), 3.4–4.9 (m, 6H), 5.2–6.0 (m, 2H), 7.2 (s, 5H).

The hydrochloride can also be obtained by converting the trifluoroacetate from Example 8 with weakly basic ion exchangers (acetate form) to pH 4.0 and then treating with ethanolic hydrochloric acid and evaporating triturating with diisopropyl ether.

EXAMPLE 10

N-(1S-carboxy-3-phenylpropyl)-S-alanyl-cis-2,3,3a,4,5,7a-hexahydro[1H]indole-2R,S-endo-carboxylic acid One equivalent of potassium hydroxide and a 10% excess of 4N potassium hydroxide solution were added to a solution of 1 g of N-(1S-carboethoxy-3-phenylpropyl)-S-alanyl-cis-2,3,3a,4,5,7a-hexahydro[1H]indole-2R,S-endo-carboxylic acid in 10 ml of water. After stirring at 20° to 25° C. for 8 hours, the reaction solution was adjusted to a pH of 4 with 2N hydrochloric acid and evaporated in vacuo. The residue was taken up in ethyl acetate and the precipitated salt was filtered off. The ethyl acetate solution was evaporated and the residue was triturated with diisopropyl ether and filtered off with suction.

Yield: 0.5 g $^1$H NMR data: (after H/D exchange) 1.5 (d, 3H), 1.0–3.2 (m, 11H), 3.9–4.7 (m, 4H), 5.4–6.0 (m, 2H), 7.2 (s, 5H)

EXAMPLE 11

N-(1S-carboxy-3-phenylpropyl)-S-alanyl-cis-2,3,3a,4,5,7a-hexahydro[1H]indole-2S-endo-carboxylic acid This compound was prepared from the compound from Example 8 in analogy to the process described in Example 10.

$^1$H NMR data: 1.5•(d, 3H), 1.0–3.2 (m, 4H), 3.9–4.7 (m, 4H), 5.4–6.0 (m, 2H), 7.2 (s, 5H)

EXAMPLE 12

N-(1S-carboethoxy-3-phenylpropyl)-S-alanyl-cis-2,3,3a,4,5,7a-hexahydro[1H]indole-2R,S-exo-carboxylic acid (a) cis-2,3,3a,4,5,7a-hexahydro[1H]indole-R,S-exo-carboxylic acid This compound was prepared from ethyl N-benzoyl-cis-2,3,3a,4,5,7a-hexahydro[1H]indole-2R,S-exo-carboxylate, which is described in Example 1b, in analogy to the process described in Example 1c.

$^1$H NMR data: (after H/D exchange) 1.6–2.5 (m, 3H), 4.4 (s, 1H), 4.8 (m, 1H), 5.4 (m, 1H), 5.8 (m, 1H)

(b) N-(1S-carboethoxy-3-phenylpropyl)-S-alanyl-cis-2,3,3a,4,5,7a-hexahydro[1H]indole-2R,S-exo-carboxylic acid This compound was prepared from the compound of Example 12a and N-(1S-carboethoxy-3-phenylpropyl)-S-alanine in analogy to the process described in Example 1d.

$^1$H NMR data: (after H/D exchange) 1.0–1.5 (m, 5H), 1.6–3.4 (m, 13H), 3.5–4.8 (m, 5H), 5.2–6.0 (m, 2H) 7.2 (s, 5H).

EXAMPLE 13

N-(1S-carboethoxy-3-phenylpropyl)-S-alanyl-cis-2,3,3a,4,5,7a-hexahydro[1H]indole-2S-exo-carboxylic acid This compound is obtained from the mixture of diastereomers from Example 12b by column chromatography on silica gel, eluting with methylene chloride/methanol 9:1 (Rf: 0.6).

$^1$H NMR data: (after H/D exchange) 1.0–1.5 (d,t 5H), 1.6–3.5 (m, 13H), 3.5–4.8 (m, 5H), 5.3–6.0 (m, 2H), 7.2 (s, 5H).

EXAMPLE 14

Tert.-butyl cis-2,3,3a,4,5,7a-hexahydro[1H]indole-2R,S-exo-carboxylate

This compound was prepared from the compound from Example 12a in analogy to the process described in Example 4.

$^1$H NMR data: 1.1–2.8 (m, 8H), 1.4 (s, 9H), 3.3–4.9 (m, 2H), 5.8 (m, 2H).

EXAMPLE 15

Tert.-butyl N-(1S-carboethoxy-3-phenylpropyl)-S-alanyl-cis-2,3,3a,4,5,7a-hexahydro[1H]indole-2S-exo-carboxylate This compound was prepared from the compound from Example 14 and N-(1S-carboethoxy-3-phenylpropyl)-S-alanine in analogy to the process described in Example 5. The mixture of diastereomers was separated on silica gel with ethyl acetate/cyclohexane 2:1.
2-S-exo-tert.-butyl ester (Rf: 0.5)
2-R-exo-tert.-butyl ester (Rf: 0.4)

EXAMPLE 16

N-(1S-carboethoxy-3-phenylpropyl)-S-alanyl-cis-2,3,3a,4,5,7a-hexahydro[1H]indole-2S-exo-carboxylic acid hydrochloride A solution of 0.8 g of tert.-butyl ester from Example 15 in 5 ml of methylene chloride was saturated with dry hydrogen chloride gas and allowed to stand at 20°–25° C. for 16 hours. The solution was evaporated in vacuo; the residue was triturated with diisopropyl ether and filtered off with suction.
Yield: 600 mg
$^1$H NMR data: 0.8–3.1 (m, 17H), 3.5–4.8 (m, 6H), 5.3–6.0 (m, 2H), 7.2 (s, 5H).

EXAMPLE 17

N-(1S-carboxy-3-phenylpropyl)-S-alanyl-cis-2,3,3a,4,5,7a-hexahydro[1H]indole-2S-exo-carboxylic acid This compound was prepared from the compound from Example 16 in analogy to the process described in Example 10.

$^1$H NMR data: 1.5 (d, 3H), 0.9–3.4 (m, 11H), 3.9–4.8 (m, 4H), 5.2–5.9 (m, 2H), 7.2 (s, 5H).

EXAMPLE 18

N-(1S-carboxy-3-phenylpropyl)-S-alanyl-cis-2,3,3a,4,5,7a-hexahydro[1H]indole-2R,S-exo-carboxylic acid This compound was prepared from the compound from Example 12 in analogy to the process described in Example 10.

$^1$H NMR data: 1.5 (d, 3H), 0.9–3.4 (m, 11H), 3.8–4.8 (m, 4H), 5.2–6.0 (m, 2H), 7.2 (s, 5H).

EXAMPLE 19

N-(1S-carboethoxy-3-phenylpropyl)-S-alanyl-cis-2,3,3a,4,5,7a-hexahydro[1H]indole-2S-endo-carboxylic acid This compound is identical with the compound described in Example 2.

(a) Ethyl ester of S-allylglycine

The preparation was carried out in the manner as described in Monatshefte der Chemie 85, 1071 (1954).

(b) Ethyl ester of N-benzoyl-N-(1,3,-butadienyl)-S-allyl glycine

This compound was prepared in analogy to the process described in Example 1a.

$^1$H NMR data: 1.1–1.4 (tr, 3H), 2.7–3.1 (m, 2H), 4.0–4.5 (m, 3H), 4.8–6.8 (m, 8H), 7.3–7.6 (s, 5H)

(c) Ethyl N-benzoyl-cis-2,3,3a,4,5,7a-hexahydro[1H]indole-2S-endo-carboxylate and ethyl N-benzoyl-cis-2,3,3a,4,5,7a-hexahydro[1H]indole-2S-exo-carboxylate This mixture of diastereomers was prepared from the compound from Example 19b in analogy to the process described in Example 1b. The mixture was separated on silica gel using toluene/ethyl acetate 4:1. Rf value of the endo compound: 0.18; Rf value of the exo compound: 0.26.

$^1$H NMR data: 0.8–2.8 (m, 10H), 3.8–4.8 (m, 4H), 5.5–5.9 (broad s, 2H), 7.4 (s, 5H)

(d) Cis-2,3,3a,4,5,7a-hexahydro[1H]indole-2S-endo-carboxylic acid

This compound was prepared from the compound from Example 19c in analogy to the process described in Example 1c.

$^1$H NMR data: (D$_2$O) 1.1–2.9 (m, 7H), 3.9–4.4 (m, 2H), 5.5–6.4 (m, 2H)

(e) N-(1S-carboethoxy-3-phenylpropyl)-S-alanyl-cis-2,3,3a,4,5,7a-hexahydro[1H]indole-2S-endo-carboxylic acid This compound was prepared from the compound from Example 19d and N-(1S-carboethoxy-3-phenylpropyl)-S-alanine in analogy to the process described in Example 1d.

$^1$H NMR data: (after H/D exchange) 1.0–2.9 (m, 17H), 3.0–4.6 (m, 6H), 5.2–6.0 (m, 2H), 7.2 (s, 5H)

EXAMPLE 20

Tert.-butyl cis-2,3,3a,4,5,7a-hexahydro[1H]indole-2S-endo-carboxylate

This compound was prepared from the compound from Example 19d in analogy to the process described in Example 4.

$^1$H NMR data: 1.4 (s, 9H), 1.0–2.7 (m, 8H), 3.2–4.9 (m, 2H), 5.8 (d, 2H).

EXAMPLE 21

Tert.-butyl N-(1S-carboethoxy-3-phenylpropyl)-S-alanyl-cis-2,3,3a,4,5,7a-hexahydro[1H]indole-2S-endo-carboxylate This compound was prepared from the compound from Example 20 and N-(1S-carboethoxy-3-phenylpropyl)-S-alanine in analogy to the process described in Example 5.

$^1$H NMR data: 1.4 (s, 9H), 0.8–3.8 (m, 20H), 3.9–4.6 (m, 4H), 5.4–6.0 (m, 2H), 7.2 (s, 5H)

EXAMPLE 22

N-(1S-carboethoxy-3-phenylpropyl)-S-alanyl-cis-2,3,3a,4,5,7a-hexahydro[1H]indole-2S-exo-carboxylic acid (a) Cis-2,3,3a,4,5,7a-hexahydro[1H]indole-2S-exo-carboxylic acid This compound was prepared from the exo compound from Example 19c in analogy to the process described in Example 1c.

$^1$H NMR data: (D$_2$O) 1.0–2.8 (m, 1H), 3.6–4.4 (m, 2H), 5.5–6.4 (m, 2H)

(b) N-(1S-carboethoxy-3-phenylpropyl)-S-alanyl-cis-2,3,3a,4,5,7a-hexahydro[1H]indole-2S-exo-carboxylic acid This compound was prepared from the compound from Example 22a and N-(1S-carboethoxy-3-phenylpropyl)-S-alanine in analogy to the process described in Example 1d.

$^1$H NMR data: (after H/D exchange) 1.0–2.9 (m, 17H), 3.0–4.6 (m, 6H), 5.2–6.0 (m, 2H), 7.2 (s, 5H)

EXAMPLE 23

Tert.-butyl cis-2,3,3a,4,5,7a-hexahydro[1H]indole-2S-exo-carboxylate

This compound was prepared from the compound from Example 22a in analogy to the process described in Example 4.

$^1$H NMR data: 1.4 (s, 9H), 0.9–2.8 (m, 8H), 3.3–4.9 (m, 2H), 5.4–5.8 (m, 2H),

EXAMPLE 24

Tert.-butyl N-(1S-carboethoxy-3-phenylpropyl)-S-alanyl-cis-2,3,3a,4,5,7a-hexahydro[1H]indole-2S-exo-carboxylate This compound was prepared from the compound from Example 23 and N-(1S-carboethoxy-3-phenylpropyl)-S-alanine in analogy to the process described in Example 5.

$^1$H NMR data: 1.3 (s, 9H), 0.9–3.7 (m, 20H), 3.8–4.7 (m, 4H), 5.4–6.0 (m, 2H), 7.2 (s, 5H)

EXAMPLE 25

Tert.-butyl N-(1S-carboethoxy-3-phenyl-3-oxopropyl)-S-alanyl-cis-2,3,3a,4,5,7a-hexahydro[1H]indole-2S-endo-carboxylate 2.5 g of N-(1S-carboethoxy-3-phenyl-3-oxopropyl)-S-alanine, together with 1.2 g of 1-hydroxybenzotriazole, 2.5 g of tert.-butyl cis-2,3,3a,4,5,7a-hexahydro[1H]indole-2S-endo-carboxylate and 2 g of dicyclohexylcarbodiimide in 20 ml of dimethylformamide were stirred at 0° C. for 1 hour and then at 20°–25° C. for 12 hours. The reaction solution was diluted with 25 ml of ethyl acetate. The precipitated urea was filtered off with suction. After evaporation in vacuo, the residue obtained was taken up in ether, the ethereal solution was washed with saturated aqueous sodium bicarbonate and with water, dried and evaporated.

Yield: 2.5 g $^1$H NMR data: 1.2 (s, 9H), 0.9–2.9 (m, 15H), 3.4–5.0 (m, 6H), 5.2–6.0 (m, 2H), 7.2–8.2 (m, 5H)

EXAMPLE 26

Tert.-butyl N-(1S-carboethoxy-3-phenyl-3-oxopropyl)-S-alanyl-cis-2,3,3a,4,5,7a-hexahydro[1H]indole-2S-exo-carboxylate This compound was prepared from the compound from Example 23 and N-(1S-carboethoxy-3-phenyl-3-oxopropyl)-S-alanine in analogy to the process described in Example 25.

$^1$H NMR data: 1.3 (s, 9H), 1.0–2.8 (m, 15H), 3.3–4.9 (m, 6H), 5.3–6.0 (m, 2H), 7.2–8.2 (m, 5H)

EXAMPLE 27

N-(1S-carboethoxy-3-phenyl-3-oxopropyl)-S-alanyl-cis-2,3,3a,4,5,7a-hexahydro[1H]indole-2S-endo-carboxylic acid trifluoroacetate 1.3 g of the compound from Example 25 were stirred in 5 ml of trifluoroacetic acid at 20°–25° C. for 2 hours. The solution was evaporated in vacuo, and the residue was triturated with diisopropyl ether and filtered off with suction.

Yield: 0.4 g $^1$H NMR data: (after H/D exchange) 1.0–3.6 (m, 15H), 3.9–4.6 (m, 6H), 5.2–5.9 (m, 2H), 7.3–8.1 (m, 5H)

EXAMPLE 28

N-(1S-carboethoxy-3-phenyl-3-oxopropyl)-S-alanyl-cis-2,3,3a,4,5,7a-hexahydro[1H]indole-2S-exo-carboxylic acid hydrochloride 0.5 g of the compound from Example 26 was dissolved in 5 ml of methylene chloride, the solution was saturated with hydrogen chloride gas and allowed to stand at 20°–25° C. for 16 hours. It was evaporated in vacuo and the residue triturated with diisopropyl ether and filtered off with suction.

Yield: 0.3 g $^1$H NMR data: (after H/D exchange) 0.9–3.5 (m, 15H), 3.9–4.8 (m, 6H), 5.3–6.0 (m, 2H), 7.1–8.0 (m, 5H)

EXAMPLE 29

N-(1S-carboxy-3-phenyl-3-oxopropyl)-S-alanyl-cis-2,3,3a,4,5,7a-hexahydro[1H]indole-2S-endo-carboxylic acid 0.5 g of the compound from Example 27 were reacted with 2 equivalents of potassium hydroxide in analogy to the procedure described in Example 10.
Yield: 0.25 g
$^1$H NMR data: (after H/D exchange) 1.1–3.6 (m, 12H), 3.7–4.6 (m, 4H), 5.2–5.9 (m, 2H), 7.1–8.0 (m, 5H)

EXAMPLE 30

N-(1S-carboxy-3-phenyl-3-oxopropyl)-S-alanyl-cis-2,3,3a,4,5,7a-hexahydro[1H]indole-2S-exo-carboxylic acid 0.5 g of the compound from Example 28 were reacted with 2 equivalents of potassium hydroxide in analogy to the procedure described in Example 10.
Yield: 0.3 g
$^1$H NMR data: (after H/D exchange) 1.0–3.5 (m, 12H), 3.6–4.8 (m, 4H), 5.2–5.9 (m, 2H), 7.2–8.0 (m, 5H)

EXAMPLE 31

Tert.-butyl S-alanyl-cis-2,3,3a,4,5,7a-hexahydro[1H]indole-2S-endo-carboxylate (a) Tert.-butyl N-methylsulfonylethyloxycarbonyl (MSC)-S-alanyl-cis-2,3,3a,4,5,7a-hexahydro[1H]indole-2S endo-carboxylate 6.7 g of 1-hydroxybenzotriazole and 14.7 g of tert.-butyl cis-2,3,3a,4,5,7a-hexahydro[1H]indole-2S-endo-carboxylate were added to a solution of 10 g of MSC-ala-OH in 50 ml of dimethylformamide. The pH was adjusted to 8.0 with N-ethylmorpholine. The mixture was cooled in an ice bath and 10.5 g of dicyclohexylcarbodiimide were added. The mixture was stirred at 20°–25° C. for 15 hours. The precipitated urea was filtered off with suction, the filtrate was evaporated in vacuo and taken up in ethyl acetate. The organic phase was washed consecutively with potassium bisulfate, potassium bicarbonate and sodium chloride solution, dried and evaporated. The residue was chromatographed on silica gel with ethyl acetate/cyclohexane 1:1.
Yield: 10 g
$^1$H NMR data: 1.4 (s, 9H), 1.3 (d, 3H), 1.1–2.6 (m, 7H), 3.0 (s, 3H), 3.2–3.5 (m, 2H), 3.5–4.9 (m, 5H), 5.6–5.9 (m, 2H)

(b) Tert.-butyl S-alanyl-cis-2,3,3a,4,5,7a-hexahydro[1H]indole-2S-endo-carboxylate 2.0 g of the compound from Example 31a were dissolved in 15 ml of methanol and 1.5 ml of water. The pH was adjusted to 13 with 2N sodium hydroxide solution and the mixture was stirred at room temperature for 2 hours. It was then neutralized with 2N hydrochloric acid, the methanol was evaporated off in vacuo and the aqueous phase was extracted with ethyl acetate, the ethyl acetate solution was washed with water, dried and evaporated. The residue was filtered through silica gel, eluting with ethyl acetate.
Yield: 0.8 g
$^1$H NMR data: 1.4 (s, 9H), 1.3 (d, 3H), 1.0–2.4 (m, 7H), 3.5–4.8 (m, 3H), 5.5–5.9 (m, 2H)

EXAMPLE 32

Tert.-butyl S-alanyl-cis-2,3,3a,4,5,7a-hexahydro[1H]indole-2S-exo-carboxylate

This compound was prepared from the compound from Example 23 in analogy to the process described in Example 31.
$^1$H NMR data: 1.2 (d, 3H), 1.4 (s, 9H), 0.9–2.3 (m, 7H), 3.4–4.7 (m, 3H), 5.6–5.9 (m, 2H)

EXAMPLE 33

Tert.-butyl N-(1S-carboethoxy-3-oxo-3-phenylpropyl)-S-alanyl-cis-2,3,3a,4,5,7a-hexahydro[1H]indole-2S-endo-carboxylate 5 mmoles of the compound from Example 31b, together with 5 mmoles of ethyl 3-benzoylacrylate and 5 drops of triethylamine, were dissolved in 50 ml of anhydrous ethanol and the mixture was stirred at 20°–25° C. for 24 hours. It was evaporated to dryness and the residue was taken up in ethyl acetate. It was then washed with water, dried and evaporated.
The mixture of diastereomers was chromatographed on silica gel, eluting with ethyl acetate/cyclohexane. The $^1$H NMR data agree with the data of the compound from Example 25.

EXAMPLE 34

Tert.-butyl N-(1S-carboethoxy-3-oxo-3-phenylpropyl)-S-alanyl-cis-2,3,3a,4,5,7a-hexahydro[1H]indole-2S-exo-carboxylate This compound was prepared from the compound from Example 32 with ethyl benzoylacrylate in analogy to the process described in Example 33.

EXAMPLE 35

Tert.-butyl N-(1S-carboethoxy-3-phenylpropyl)-S-alanyl-cis-2,3,3a,4,5,7a-hexahydro[1H]indole-2S-endo-carboxylate 5 mmoles of tert.-butyl S-alanyl-cis-2,3,3a,4,5,7a-hexahydro[1H]indole-2S-endo-carboxylate were dissolved in 15 ml of anhydrous ethanol. The pH of the solution was adjusted to 7.0 with ethanolic potassium hydroxide, and 0.7 g of powdered molecular sieves (4 Å) and then 5 mmoles of ethyl 2-keto-4-phenylbutyrate were added. A solution of 0.6 g of sodium cyanoborohydride in 6 ml of anhydrous ethanol was slowly added dropwise. After a reaction time of 20 hours at 20° to 25° C., the solution was filtered and the solvent was distilled off. The residue was taken up in ethyl acetate/water. After evaporation of the ethyl acetate phases, the residue was chromatographed on silica gel with ethyl acetate/cyclohexane 1:4.
The $^1$H NMR data agree with the data of the compound from Example 21.

EXAMPLE 36

Tert.-butyl N-(1S-carboethoxy-3-phenylpropyl)-S-alanyl-cis-2,3,3a,4,5,7a-hexahydro[1H]indole-2S-exo-carboxylate This compound was prepared from the compound from Example 32 and ethyl 2-keto-4-phenylbutyrate in analogy to the process described in Example 35.

EXAMPLE 37

Tert.-butyl N-(1S-carboethoxy-3-oxo-3-phenylpropyl)-S-alanyl-cis-2,3,3a,4,5,7a-hexahydro[1H]indole-2S-endo-carboxylate 10 mmoles of acetophenone, 10 mmoles of ethyl glyoxylate and 10 mmoles of tert.-butyl S-alanyl-cis-2,3,3a,4,5,7a-hexahydro[1H]indole-2S-endo-carboxylate in 30 ml of glacial acetic acid were heated at 45° C. for 36 hours. After evaporation in vacuo, the residue was neutralized with sodium bicarbonate solution and extracted with ethyl acetate. The ethyl acetate phase was evaporated and chromatographed on silica gel, eluting with ethyl acetate/cyclohexane 1:1.

The $^1$H NMR data agree with the data of the compound from Example 25.

EXAMPLE 38

Tert.-butyl N-(1S-carboethoxy-3-oxo-3-phenylpropyl)-S-alanyl-cis-2,3,3a,4,5,7a-hexahydro[1H]indole-2S-exo-carboxylate This compound was prepared from the compound from Example 32 and ethyl glyoxylate and acetophenone in analogy to the process described in Example 37.

The $^1$H NMR data agree with the data of the compound from Example 24.

EXAMPLE 39

N-(1S-carboethoxy-3R,S-hydroxy-3-phenylpropyl)-S-alanyl-cis-2,3,3a,4,5,7a-hexahydro[1H]indole-2S-endo-carboxylic acid 0.5 g of N-(1S-carboethoxy-3-oxo-3-phenylpropyl)-S-alanyl-cis-2,3,3a,4,5,7a-hexahydro[1H]indole-2S-endocarboxylic acid were dissolved in 5 ml of aqueous ethanol, and 0.1 g of sodium borohydride was added. The mixture was stirred at room temperature for 14 hours. Then ethyl acetate was added, and the ethyl acetate solution was washed with water, dried and evaporated. The crude product was filtered through silica gel, eluting with ethyl acetate/methanol 9:1.

Yield: 0.3 g $^1$H NMR data: (after H/D exchange) 1.0–3.5 (m, 15H), 3.8–4.8 (m, 7H), 5.3–5.8 (m, 2H), 7.2 (s, 5H)

EXAMPLE 40

N-(1S-carboethoxy-3R,S-hydroxy-3-phenylpropyl)-S-alanyl-cis-2,3,3a,4,5,7a-hexahydro[1H]indole-2S-exo-carboxylic acid 0.5 g of N-(1S-carboethoxy-3-oxophenylpropyl)-S-alanyl-cis-2,3,3a,4,5,7a-hexahydro[1H]indole-2S-exo-carboxylic acid were reacted with 0.1 g of sodium borohydride in analogy to the process described in Example 39.

Yield: 0.2 g $^1$H NMR data (after H/D exchange) 0.9–3.4 (m, 15H), 3.7–4.9 (m, 7H), 5.2–5.9 (m, 2H), 7.2 (s, 5H).

We claim:

1. A compound of the formula III,

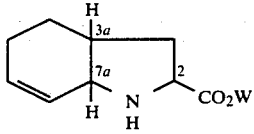

in which
the H atoms on the C atoms 3a and 7a have the cis-configuration relative to one another and the group —CO$_2$W on the C atom 2 is oriented exo or endo to the bicyclic ring system and wherein W denotes hydrogen or (C$_1$–C$_6$)-alkyl or aralkyl having 7 to 9 C atoms.

2. A process for the preparation of a compound of the formula III as claimed in claim 1, by treating a compound of the formula IX,

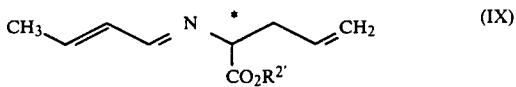

in which
R$^{2'}$ denotes (C$_1$–C$_6$)-alkyl or (C$_7$ to C$_8$)-aralkyl, with an acylating agent, of the formula Cl—CO—R$^3$, wherein the radical R$^3$ represents (C$_1$ to C$_6$)-alkyl, (C$_5$ to C$_9$)-cycloalkyl, (C$_2$ to C$_6$)-alkenyl, (C$_1$ to C$_6$)-alkoxy, aryl, aryloxy, aryl-(C$_1$ to C$_4$)-alkyl or aryl-(C$_1$ to C$_4$)-alkoxy, to give a compound of the formula X,

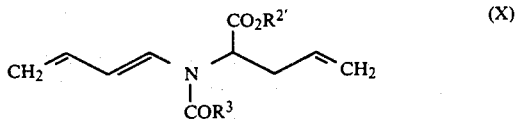

in which
R$^{2'}$ and R$^3$ have the foregoing meaning, heating this in an organic solvent which boils in a temperature range between 80° and 250° C. to give a mixture of stereoisomeric compounds of the formula XI

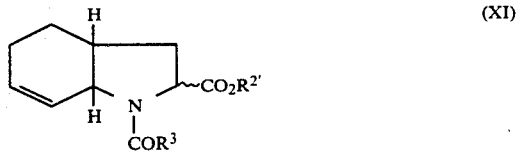

in which
R$^{2'}$ and R$^3$ have the foregoing meaning and the hydrogen atoms on the bridgehead C atoms have the cis configuration, treating this mixture of stereoisomers with aqueous acid or alkali.

3. A process as claimed in claim 2, wherein the mixture of stereoisomers of the formula XI is separated into enantiomers, pairs of diastereomers or racemates.

4. A process as claimed in claim 3, wherein the compound of the formula III, in which W represents hydrogen is esterified to give a compound in which W represents (C$_1$–C$_6$)-alkyl or aralkyl having 7 to 9 C atoms.

5. A process as claimed in claim 2, wherein the compound of the formula III, in which W represents hydrogen is esterified to give a compound in which W represents (C$_1$–C$_6$)-alkyl or aralkyl having 7 to 9 C atoms.